(12) United States Patent
Tah

(10) Patent No.: US 11,399,702 B2
(45) Date of Patent: Aug. 2, 2022

(54) URETEROSCOPE DEVICE AND METHOD FOR USING OF SUCH A DEVICE

(71) Applicant: Boston Scientific Scimed, Inc., Maple Grove, MN (US)

(72) Inventor: Richard C. Tah, Milford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 315 days.

(21) Appl. No.: 16/707,619

(22) Filed: Dec. 9, 2019

(65) Prior Publication Data

US 2020/0196834 A1 Jun. 25, 2020

Related U.S. Application Data

(60) Provisional application No. 62/782,566, filed on Dec. 20, 2018.

(51) Int. Cl.
| | | |
|---|---|---|
| *A61B 1/005* | (2006.01) | |
| *A61B 1/00* | (2006.01) | |
| *A61B 1/307* | (2006.01) | |

(52) U.S. Cl.
CPC ........ *A61B 1/0052* (2013.01); *A61B 1/00098* (2013.01); *A61B 1/307* (2013.01)

(58) Field of Classification Search
CPC .... A61B 1/0052; A61B 1/00098; A61B 1/307
See application file for complete search history.

(56) References Cited

U.S. PATENT DOCUMENTS

| | | | | |
|---|---|---|---|---|
| 8,992,470 | B2 * | 3/2015 | Barenboym | A61M 25/0147 604/95.04 |
| 2007/0203474 | A1 * | 8/2007 | Ryan | A61M 25/0662 604/528 |
| 2009/0234280 | A1 | 9/2009 | Tah et al. | |
| 2013/0144125 | A1 * | 6/2013 | Konstorum | A61B 1/0011 600/150 |
| 2013/0237907 | A1 * | 9/2013 | Bacher | A61B 17/2909 604/95.04 |
| 2016/0374536 | A1 | 12/2016 | Osaki | |

FOREIGN PATENT DOCUMENTS

| | | |
|---|---|---|
| EP | 2 799 001 | 11/2014 |
| KR | 2016-0042225 | 4/2016 |
| WO | 2014/115068 | 7/2014 |

* cited by examiner

*Primary Examiner* — Alexandra L Newton
*Assistant Examiner* — Rynae E Boler
(74) *Attorney, Agent, or Firm* — Fay Kaplun & Marcin, LLP

(57) ABSTRACT

A medical device includes a sheath extending longitudinally from a proximal end to a distal end and a handle coupled to the proximal end of the sheath. The handle includes a deflection lever coupled thereto. The deflection lever is rotatable proximally and distally along the handle to deflect a distal end of the shaft to which it is operably coupled and a locking mechanism movable between an locked configuration in which the locking mechanism engages an engagement feature on the outer surface of the handle, preventing the deflection lever from rotating and locking the distal end of the shaft in a desired position, and an unlocked configuration in which the locking mechanism releases the engagement feature to allow rotation of the deflection lever and deflection of the distal end of the shaft.

13 Claims, 2 Drawing Sheets

URETEROSCOPE DEVICE AND METHOD FOR USING OF SUCH A DEVICE

PRIORITY CLAIM

The present disclosure claims priority to U.S. Provisional Patent Application Ser. No. 62/782,566 filed Dec. 20, 2018; the disclosure of which is incorporated herewith by reference.

FIELD

Aspects of the present disclosure generally relate to medical devices and methods. Particular aspects relate generally to ureteroscope devices and methods for the use of such scopes.

BACKGROUND

Flexible ureteroscopes are often used in the examination of kidneys and are generally incorporated with features to improve accessibility and patient comfort. Flexible ureteroscopes are generally provided with a flexible tip section that is controlled by the physician through manipulation of a lever attached to the handle of the scope. Such manipulation enables the physician to maneuver the tip of the scope to different locations such as, for example, different calyces within the kidney. Ureteroscopes are typically used in conjunction with other devices for the treatment of ailments of the kidney. As an example, urologists often use the LithoVue™ flexible ureteroscope in combination with a basket to pulverize kidney stones and remove the debris from the body. Such procedures require manipulating a lever on the ureteroscope to control the tip of the scope and can be very tiring on the physician's hand and the thumb. Sometimes it is desired to hold the tip of the ureteroscope in a location, (e.g., with the tip directed toward a target stone), while the physician operates other devices to remove the stone. Holding the scope in a specific location/orientation by holding the lever in one place requires holding the lever in one place potentially leading to thumb fatigue. Some ureteroscopes incorporate a locking lever which needs to be actuated using the physician's other hand, adding complexity to the procedure by requiring the physician to perform yet another action to lock the tip of the scope.

SUMMARY

The present disclosure relates to a medical device, comprising a sheath extending longitudinally from a proximal end to a distal end and a handle coupled to the proximal end of the sheath. The handle includes a deflection lever coupled thereto, the deflection lever being rotatable proximally and distally along the handle to deflect a distal end of the shaft to which it is operably coupled and a locking mechanism movable between an locked configuration in which the locking mechanism engages an engagement feature on the outer surface of the handle, preventing the deflection lever from rotating and locking the distal end of the shaft in a desired position, and an unlocked configuration in which the locking mechanism releases the engagement feature to allow rotation of the deflection lever and deflection of the distal end of the shaft.

In an embodiment, the deflection lever may include a slot extending therethrough.

In an embodiment, the locking mechanism may include a locking lever including a lever body and a locking tooth, the lever body configured to be positioned within the slot such that the locking tooth engages the engagement mechanism with a portion of the lever body protruding out of the slot when the locking mechanism is in the locked configuration.

In an embodiment, the locking mechanism may further include a spring configured to bias the locking mechanism to the locked configuration, a first end of the spring being coupled to the locking lever and a second end of the spring being coupled to the deflection lever such that depression of the lever body further into the slot causes the lever body to pivot, releasing the locking tooth from the engagement mechanism and moving the locking mechanism to the unlocked configuration.

In an embodiment, the engagement mechanism may be a plurality of indentations, the plurality of indentations configured to receive the locking tooth therein when the locking mechanism is in the locked configuration.

In an embodiment, the deflection lever may be coupled to a first lateral side of the handle.

In an embodiment, the deflection lever may be substantially arced in shape and extends from the first lateral side of the handle toward an opposing second lateral side of the handle.

In an embodiment, the locking lever may be substantially arced in shape.

In an embodiment, the deflection lever may rotate around a rounded proximal corner of the handle.

In an embodiment, the locking lever may include a pivot hole, the biasing spring being coupled to the pivot hole such that, when the lever body is depressed by an external force, the lever body rotates about the pivot hole to release the locking tooth from the plurality of indentations.

The present disclosure also relates to a medical device, comprising a sheath extending longitudinally from a proximal end to a distal end and a handle coupled to the proximal end of the sheath, the handle including a lever assembly actuatable via a single hand of a user to manipulate the shaft. The lever assembly includes a deflection lever coupled to a proximal portion of the handle, the deflection lever being rotatable proximally and distally to deflect a distal end of the shaft to which it is operably coupled and a locking mechanism biased toward a locked configuration in which a portion of the locking mechanism engages an engagement feature on the outer surface of the handle, preventing the deflection lever from rotating and locking the distal end of the shaft in a desired position, and an unlocked configuration in which the locking mechanism releases the engagement feature to allow rotation of the deflection lever and deflection of the distal end of the shaft.

In an embodiment, the locking mechanism may include a locking lever including a lever body and a locking tooth, the lever body configured to be positioned within a slot extending through the deflection lever such that the locking tooth engages the engagement mechanism with a portion of the lever body protruding out of the slot when the locking mechanism is in the locked configuration.

In an embodiment, the locking mechanism may further include a spring configured to bias the locking mechanism to the locked configuration, a first end of the spring being coupled to the locking lever and a second end of the spring being coupled to the deflection lever such that depression of the lever body further into the slot causes the lever body to pivot, releasing the locking tooth from the engagement mechanism and moving the locking mechanism to the unlocked configuration.

In an embodiment, the locking lever may include a pivot hole, the biasing spring being coupled to the pivot hole such that, when the lever body is depressed by an external force, the lever body rotates about the pivot hole to release the locking tooth from the plurality of indentations.

In an embodiment, the engagement mechanism may be a plurality of indentations, the plurality of indentations configured to receive the locking tooth therein when the locking mechanism is in the locked configuration.

BRIEF DESCRIPTION

DETAILED DESCRIPTION

Figure 1:
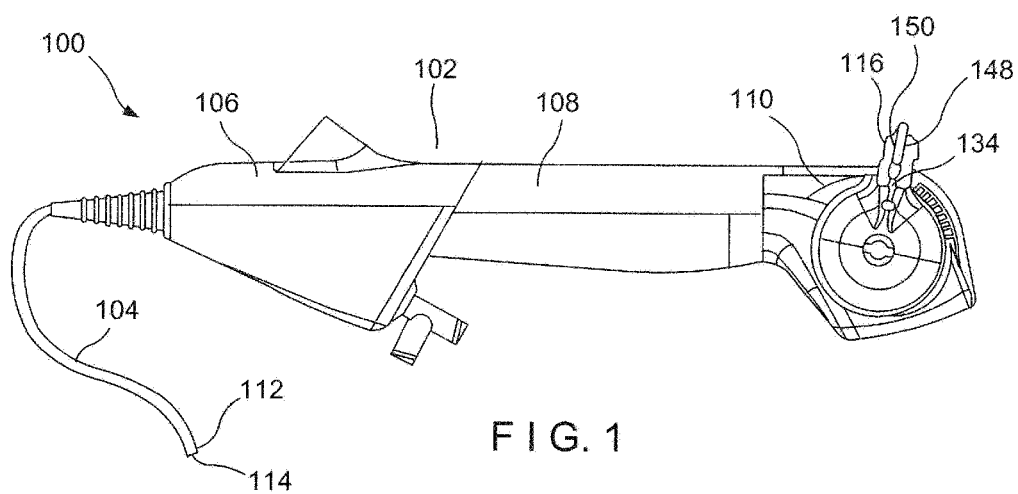
FIG. 1 shows a side view of a scope device according to an exemplary embodiment of the present disclosure.

The present disclosure may be further understood with reference to the following description and appended drawings, wherein like elements are referred to with the same reference numerals. The present disclosure relates to a medical device and a method of using such a device. In particular, the present disclosure relates to, for example, to devices and methods for passively locking a distal end of a shaft of a scope device. Exemplary embodiments describe a system including a locking mechanism positioned on an endoscope or ureteroscope device, such as the LithoVue™. In these embodiments, the locking mechanism need only be manipulated with a single thumb of the physician. It should be noted that the terms "proximal" and "distal", as used herein, are intended to refer to a direction toward (proximal) and away from (distal) a user of the device (e.g., physician).

As shown in FIGS. 1-6, a scope device 100 according to an exemplary embodiment of the present embodiment comprises, in an exemplary embodiment, a handle 102 which, during use, remains outside a living body and a shaft 104 configured to be inserted through a target lumen to a target site within the body. As shown in FIG. 1, the scope device 100 may comprise any scope configured for use in minimally invasive procedures, such as a ureteroscope, for example, under the brand name LithoVue™ or Next Generation LithoVue™, an endoscope, a hysteroscope, a bronchoscope, a cystoscope, or any similar device. The handle 102 includes a distal portion 106, an intermediate portion 108 and a proximal portion 110. As shown in FIG. 1, the curvature of the handle 102 defines the proximal portion 110. A distal end of the distal portion 106 is connected to a proximal end of the shaft 104, which extends distally therefrom to a shaft distal end 112. The distal end 112 of the shaft 104 may be steered through movement of a deflection lever mechanism 116 at the proximal portion 110 of the handle 102.

Figure 2:
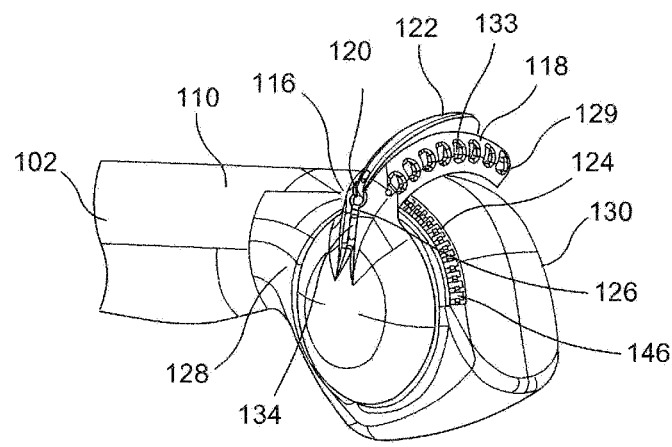
FIG. 2 shows a perspective view of a deflection lever and locking mechanism of the scope device of FIG. 1 according to an exemplary embodiment of the present disclosure.

The proximal portion 110 of the handle 102 may be sized and shaped to provide a form-fitting shape to be ergonomically held by a user's hand. The deflection lever mechanism 116, as shown in FIG. 2, may be coupled to one lateral side of the handle 102. For example, the deflection lever mechanism 116 may be positioned on a rounded corner portion of the proximal portion 110. Then, when the handle 102 is held by a user, the user's thumb may manipulate the deflection lever mechanism 116 by subjecting a force, either proximally or distally, to cause rotational movement along the rounded corner portion of the proximal portion 110 of the handle 102. The deflection lever mechanism 116 includes a deflection lever 118 and a locking mechanism 120 comprising a locking lever 122, a serrated section 124 of the proximal portion 110 of the handle 102, and a biasing spring 126 (shown in greater detail in FIG. 6).

The deflection lever 118, as shown in FIG. 2, is a rotatable lever rotatably coupled to a first lateral side 128 of the handle 102. The deflection lever 118 extends from the first lateral side 128 of the handle 102 over the proximal portion 110 toward a free end 129 at a second lateral side 130 of the handle 102. As noted above, the deflection lever 118 is rotatable proximally and distally along the rounded corner portion of the proximal portion 110 to steer the distal end 112 of the shaft 104 as desired. The deflection lever 118 may include gripping features 132 such as ridges or cutouts 133 to help the user's thumb manipulate the lever 118 as desired. The deflection lever 118 includes a slot 134 extending therethrough from the first lateral side 128 to the free end 129 of the deflection lever 118 and is configured to receive the locking lever 122 and the biasing spring 126 therein, as will be described in further detail below. In an exemplary embodiment, shown in FIG. 2, the deflection lever 118 may be substantially rounded or arc-shaped from the first lateral side 128 to the free end 129, following the contour of the outer surface of the proximal portion 110. This arced contour of the deflection lever 118 allows for easier gripability and maneuverability by the user when in use.

Figure 3:
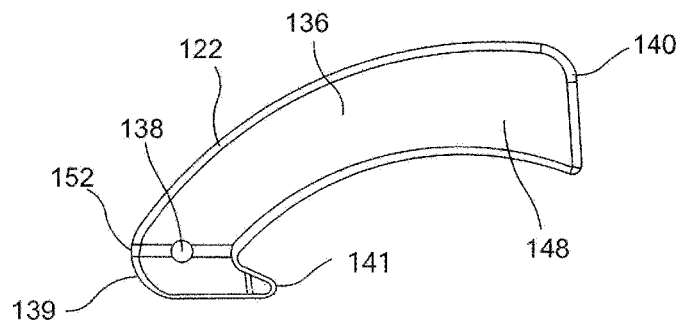
FIG. 3 shows a side view of a locking lever of the locking mechanism of FIG. 2.
Figure 4:
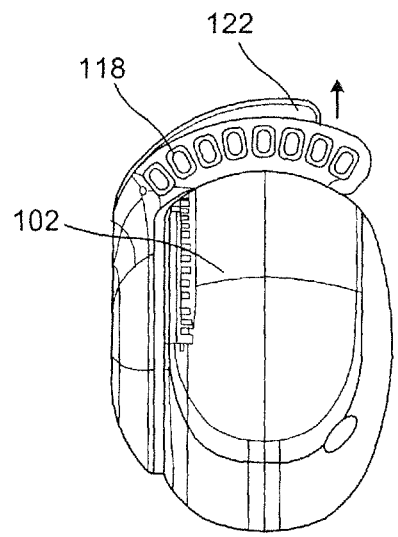
FIG. 4 shows a back view of the locking mechanism of FIG. 2 in the engaged configuration.
Figure 5:
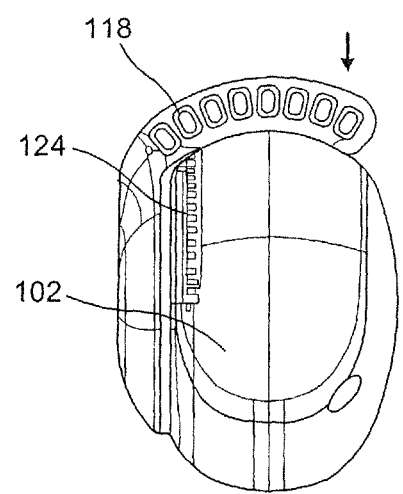
FIG. 5 shows a back view of the locking mechanism of FIG. 2 in the disengaged configuration.
Figure 6:
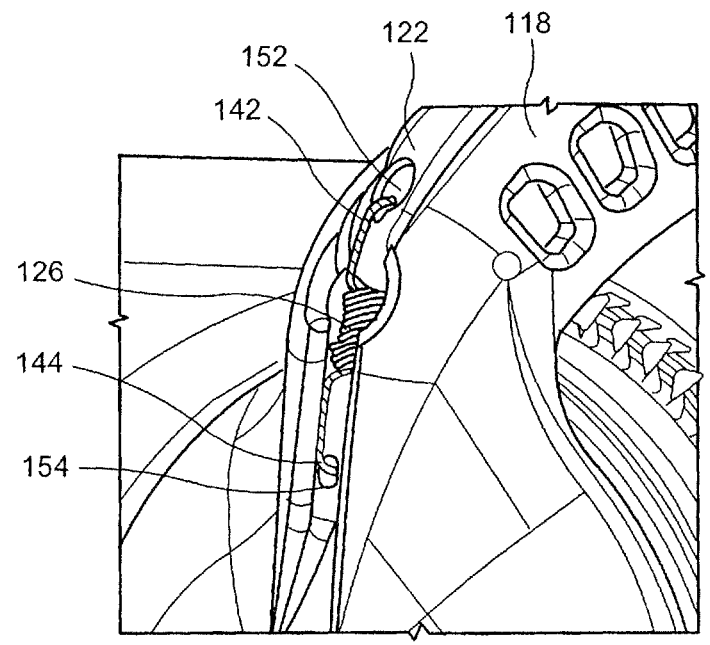
FIG. 6 shows a perspective view of the biasing spring of the locking mechanism of FIG. 2, according to an exemplary embodiment of the present disclosure.

The locking lever 122, as better shown in FIG. 3, includes a lever body 136, a pivot hole 138 and a locking tooth locking tooth 141. The lever body 136 is substantially flat and is sized and shaped to be inserted into the slot 134 of the deflection lever 118. Similar to the deflection lever 118, the lever body 136 may be substantially rounded or arc-shaped from a first lateral end 139 to a second lateral end 140 to follow the contour of the outer surface of the proximal portion 110 of the handle 102. This arced shape of the lever body 136 allows for smoother maneuverability over the outer surface of the handle 102. As can be seen in FIGS. 4-5, the arced shape of the lever body 136 is substantially similar to the arced shape of the deflection lever 118.

However, the lever body 136 is positioned within the slot 134 so that it protrudes past a top surface (i.e., a surface opposing a surface facing the outer surface of the handle 102) of the deflection lever 118 when in a resting, or normal, state, shown in FIG. 4. As will be described in further detail below, this positioning of the locking lever 122 provides space between a bottom surface of the locking lever 122 (i.e., a surface facing the outer surface of the handle 102) and the outer surface of the handle 102 such that the lever 122 may be depressed (i.e., pivoted about the pivot hole 138), as shown in FIG. 4, to release the locking lever 122 from the serrated section 124 of the handle 102. Furthermore, when the locking lever 122 is depressed, releasing the locking tooth 141 from the serrated section 124, the user's thumb is in contact with both the locking lever 122 and the deflection lever 118, enabling the levers 122, 118 to be moved, or rotated, together.

The lever body 136 of the locking lever 122 includes the pivot hole 138 extending therethrough from a substantially planar proximal surface 148 thereof to a substantially planar distal surface 150 thereof. A pin (not shown) extends across the slot 134 of the deflection lever 118 and through the pivot hole 138 to pivotally couple the lever body 136 to the deflection lever 118. Thus, when the locking lever 122 is depressed to move the locking lever from an engaged state, in which the locking tooth 141 engages an indentation 146 in the serrated section 124 (locking deflection lever mechanism 116 in place), to a released state, in which the locking tooth 141 is rotated out of the indentation 146 to be released from the serrated section 124 of the handle 102, the locking lever 122 pivots about an axis of the pivot hole 138. While the locking lever 122 is depressed and in the released state, the deflection lever mechanism 116 may be rotated to change a steering angle of the distal end 112 of the shaft 104.

In particular, the locking tooth 141 extends from the lever body 136 toward the first lateral side 128 of the proximal portion 110 of the handle 102 to engage the serrated section 124 of the handle 102. When in an engaged state, the locking tooth 141 engages one of the indentations 146 of the serrated section 124 to lock the locking lever 122 in position, thereby locking the deflection lever 118 and the distal end 112 of the shaft 104 in a desired position. Depression of the lever body 136 by the user, however, causes the lever body 136 to rotate about the pivot hole 138, moving the locking tooth 141 out of the serrated section 124, unlocking the deflection lever 118 until the lever body 136 is released.

The lever body 136 may be biased toward the engaged configuration via the biasing spring 126 which, in this embodiment, is an extension spring. It will be understood by those skilled in the art, however, that the biasing spring 126 may be any type of spring member such as, for example, a torsion spring, or even a molded part of the locking mechanism 120. The biasing spring 126 may extend from a first end 142 to a second end 144 and is configured so that in a normal, or un-extended, state, the biasing spring 126 engages the locking tooth 141 with the serrated section 124. The first end 142 is passed through an opening 152 extending into the first lateral side 139 of the lever body 136 to form a loop thereabout while the second end 144 is passed through a connection hole 154 in the deflection lever 118 to form a loop thereabout. It will be understood, however, that the biasing spring 126 maybe coupled to the lever body 136 and the deflection lever 118 in any suitable manner such that the locking tooth 141 engages the serrated section 124 when the spring is in its normal state.

The serrated section 124 longitudinally extends along the outer surface of the proximal portion 110 of the handle 102. Specifically, the serrated section 124 extends along the proximal rounded edge or corner portion of the handle 102 adjacent to the deflection lever 118 along a track followed by the locking tooth 141 as the levers 118, 122 are moved proximally and distally, as shown in FIG. 2. The serrated section 124 includes a plurality of indentations connection hole 154 that are longitudinally spaced along the serrated section 124. Each of the indentations 146 is sized and shaped to receive the locking tooth 141 therein to lock the deflection lever 118 in a position corresponding to the indentation within which the locking tooth is received. It is noted that although the embodiments of the figures describe a serrated section 124 on the handle 102 configured to engage the locking tooth 141, the handle may include any type of engagement feature such as, for example, a rough area on the handle 102 formed through, for example, a knurling finished surface.

An exemplary method of use of the scope device 100 includes inserting the distal end 112 of the shaft 104 into a target lumen and advancing the shaft 104 therethrough to a target cavity within, for example, the kidney. During insertion, the distal end 112 may be locked in a substantially straight position. Once the shaft 104 has been positioned within the kidney as desired, the user may depress the locking lever 122 with his thumb such that the locking tooth 141 is rotated out of the serrated section 124. The levers 118, 122 may then be moved proximally and distally by the user's thumb as desired. This proximal/distal movement allows the user to deflect the distal end 112 of the shaft 104 to a preferred orientation within the target cavity. Once the distal end 112 is in the preferred orientation, the user may release his thumb from the levers 118, 122, causing the locking tooth 141 to rotate into a corresponding one of the indentations 146, locking the distal end 112 in position. At any point, the user may change the position of the distal end 112 by repeating the described method.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A medical device, comprising:
a sheath extending longitudinally from a proximal end to a distal end; and
a handle coupled to the proximal end of the sheath, the handle including:
a deflection lever coupled thereto, the deflection lever being rotatable proximally and distally along the handle to deflect a distal end of the shaft to which it is operably coupled, wherein the deflection lever includes a slot extending therethrough; and
a locking mechanism including a pivotable locking lever including a lever body and a locking tooth rigidly connected to and extending from the lever body, the lever body configured to be positioned within the slot, the locking mechanism configured to be pivoted relative to the deflection lever between a locked configuration in which portion of the lever body protrudes out of the slot and the locking tooth engages an engagement feature on the outer surface of the handle, preventing the deflection lever from rotating and locking the distal end of the shaft in a desired position, and an unlocked configuration in which the portion of the lever body is pushed into the slot and the locking lever is pivoted relative to the deflection lever so that the locking tooth is released from the engagement feature to allow rotation of the deflection lever and deflection of the distal end of the shaft.

2. The device of claim 1, wherein the locking mechanism further includes a spring configured to bias the locking mechanism to the locked configuration, a first end of the spring being coupled to the locking lever and a second end of the spring being coupled to the deflection lever such that depression of the lever body further into the slot causes the lever body to pivot, releasing the locking tooth from the engagement mechanism feature and moving the locking mechanism to the unlocked configuration.

3. The device of claim 1, wherein the engagement feature is a plurality of indentations, the plurality of indentations configured to receive the locking tooth therein when the locking mechanism is in the locked configuration.

4. The device of claim 1, wherein the deflection lever is coupled to a first lateral side of the handle.

5. The device of claim 1, wherein the deflection lever is substantially arced in shape and extends from the first lateral side of the handle toward an opposing second lateral side of the handle.

6. The device of claim 1, wherein the locking lever is substantially arced in shape.

7. The device of claim 1, wherein the deflection lever rotates around a rounded proximal corner of the handle.

8. The device of claim 2, wherein the locking lever includes a pivot hole, the biasing spring being coupled to the pivot hole such that, when the lever body is depressed by an external force, the lever body rotates about the pivot hole to release the locking tooth from the plurality of indentations.

9. A medical device, comprising:
a sheath extending longitudinally from a proximal end to a distal end; and
a handle coupled to the proximal end of the sheath, the handle including a lever assembly actuatable via a single hand of a user to manipulate the shaft, the lever assembly including:
a deflection lever coupled to a proximal portion of the handle, the deflection lever being rotatable proximally and distally to deflect a distal end of the shaft to which it is operably coupled, wherein the deflection lever includes a slot extending therethrough; and
a locking mechanism including a pivotable locking lever including a lever body and a locking tooth rigidly connected to and extending from the lever body, the lever body configured to be positioned within the slot, the locking mechanism configured to be biased toward a locked configuration in which a portion of the lever body protrudes out of the slot and the locking tooth engages an engagement feature on the outer surface of the handle, preventing the deflection lever from rotating and locking the distal end of the shaft in a desired position, the locking mechanism configured to be pivoted relative to the deflection lever into an unlocked configuration in which the portion of the lever body is pushed into the slot and the locking lever is pivoted relative to the deflection lever so that the locking tooth is released from the engagement feature to allow rotation of the deflection lever and deflection of the distal end of the shaft.

10. The device of claim 9, wherein the locking mechanism further includes a spring configured to bias the locking mechanism to the locked configuration, a first end of the spring being coupled to the locking lever and a second end of the spring being coupled to the deflection lever such that depression of the lever body further into the slot causes the lever body to pivot, releasing the locking tooth from the engagement feature and moving the locking mechanism to the unlocked configuration.

11. The device of claim 10, wherein the locking lever includes pivot hole, the biasing spring being coupled to the pivot hole such that, when the lever body is depressed by an external force, the lever body rotates about the pivot hole to release the locking tooth from the plurality of indentations.

12. The device of claim 9, wherein the engagement feature is a plurality of indentations, the plurality of indentations configured to receive the locking tooth therein when the locking mechanism is in the locked configuration.

13. The medical device of claim 1, wherein the slot extends laterally through the deflection lever and the locking lever extends laterally through the slot.

* * * * *